US010335170B2

(12) United States Patent
Victor et al.

(10) Patent No.: US 10,335,170 B2
(45) Date of Patent: Jul. 2, 2019

(54) CUTTING HEADS FOR INTRAMEDULLARY REAMERS

(71) Applicant: Greatbatch Ltd., Clarence, NY (US)

(72) Inventors: Gary C. Victor, Wheatfield, NY (US); Kari Ann Sausen, Clarence, NY (US); Curtis J. Schwartzkopf, Cheektowaga, NY (US)

(73) Assignee: VIANT AS&O HOLDINGS, LLC, AZ (US)

( * ) Notice: Subject to any disclaimer, the term of this patent is extended or adjusted under 35 U.S.C. 154(b) by 57 days.

(21) Appl. No.: 15/431,014

(22) Filed: Feb. 13, 2017

(65) Prior Publication Data

US 2017/0231643 A1    Aug. 17, 2017

Related U.S. Application Data

(60) Provisional application No. 62/294,642, filed on Feb. 12, 2016.

(51) Int. Cl.
*A61B 17/16* (2006.01)
*A61B 17/00* (2006.01)
(Continued)

(52) U.S. Cl.
CPC ........ *A61B 17/164* (2013.01); *A61B 17/1615* (2013.01); *A61B 17/1659* (2013.01);
(Continued)

(58) Field of Classification Search
CPC .............. A61B 17/164; A61B 17/1615; A61B 17/1659; A61B 17/162
See application file for complete search history.

(56) References Cited

U.S. PATENT DOCUMENTS 4,473,070 A * 9/1984 Matthews ............ A61B 17/164
30/352
4,706,659 A    11/1987 Matthews et al.
(Continued)

FOREIGN PATENT DOCUMENTS

CN    201862859    6/2011
DE    202012104364    4/2013
(Continued)

OTHER PUBLICATIONS

Extended European Search, Application No. 17155887.7 dated Sep. 13, 2017.
(Continued)

*Primary Examiner* — Matthew J Lawson
*Assistant Examiner* — Amy R Sipp
(74) *Attorney, Agent, or Firm* — Steven J. Grossman; Grossman Tucker Perreault & Pfleger PLLC

(57) ABSTRACT

A bone cutter for use within the intramedullary canal is described. The bone cutter comprises a frusto-conical cutting head that extends to a barrel portion for attachment to a drive shaft. The cutting head comprises a plurality of spaced apart blades having a tissue cutting edge that extends radially from the exterior surface of the cutting head. The plurality of blades are arranged at prescribed angular relationships that are designed to increase cutting efficiency and debris removal, thereby reducing reactive torque, axial loading, and head pressure during a surgical procedure.

10 Claims, 13 Drawing Sheets

(51) Int. Cl.
*B22F 3/22* (2006.01)
*B22F 3/24* (2006.01)

(52) U.S. Cl.
CPC ... *A61B 17/162* (2013.01); *A61B 2017/00526* (2013.01); *B22F 3/225* (2013.01); *B22F 3/24* (2013.01); *B22F 2003/248* (2013.01)

(56) References Cited

U.S. PATENT DOCUMENTS

| | | | |
|---|---|---|---|
| 4,751,922 A * | 6/1988 | DiPietropolo | B23Q 5/043 |
| | | | 606/80 |
| 5,122,134 A | 6/1992 | Borzone et al. | |
| 5,908,423 A * | 6/1999 | Kashuba | A61B 17/164 |
| | | | 408/127 |
| 5,968,048 A | 10/1999 | Harder | |
| 6,258,093 B1 | 7/2001 | Edwards et al. | |
| 6,918,913 B2 | 7/2005 | White et al. | |
| 6,949,101 B2 | 9/2005 | McCleary et al. | |
| 7,229,457 B2 | 6/2007 | Murphy et al. | |
| 7,803,159 B2 | 9/2010 | Perez-Cruet et al. | |
| 8,454,608 B2 | 6/2013 | White et al. | |
| 2004/0236339 A1 | 11/2004 | Pepper et al. | |
| 2004/0267266 A1 * | 12/2004 | Daniels | A61B 17/162 |
| | | | 606/80 |
| 2005/0075638 A1 | 4/2005 | Collazo et al. | |
| 2007/0184407 A1 | 8/2007 | Duesing | |
| 2008/0132929 A1 | 6/2008 | O'Sullivan et al. | |
| 2012/0253348 A1 | 10/2012 | Arlettaz et al. | |
| 2016/0199145 A1 * | 7/2016 | Haidukewych | A61B 90/06 |
| | | | 606/80 |

FOREIGN PATENT DOCUMENTS

| | | |
|---|---|---|
| EP | 1974680 | 10/2008 |
| EP | 2668931 | 12/2013 |
| WO | 200143650 | 6/2001 |
| WO | 2011113115 | 9/2011 |

OTHER PUBLICATIONS

European Partial Search report, Application 17155887.7, dated Jun. 6, 2017.

* cited by examiner

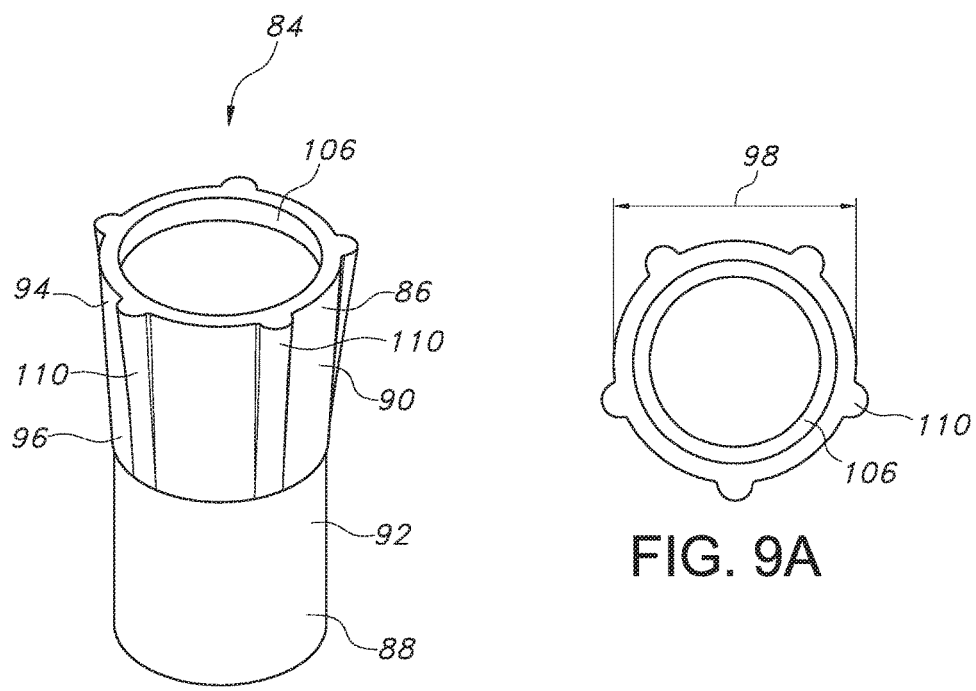
FIG. 9
FIG. 9A
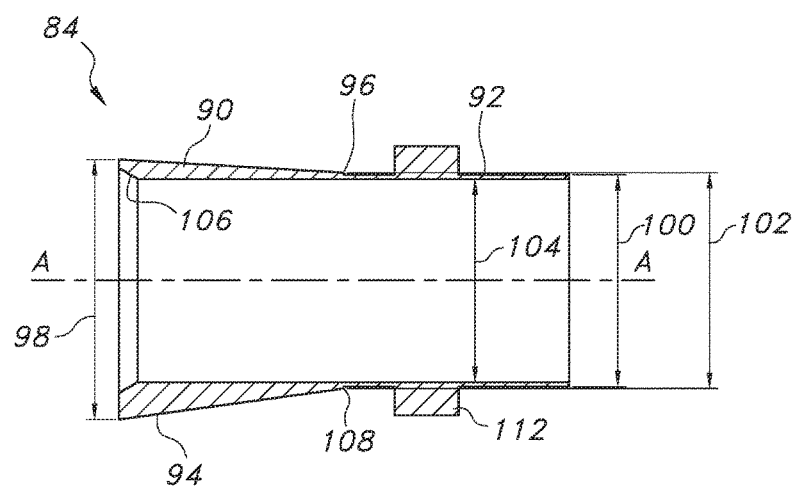
FIG. 9B

CUTTING HEADS FOR INTRAMEDULLARY REAMERS

CROSS-REFERENCE TO RELATED APPLICATION

This application claims priority from U.S. Provisional Patent Application Ser. No. 62/294,642, filed Feb. 12, 2016.

FIELD OF THE INVENTION

The present invention relates to the art of orthopedic reamers, and more particularly, to cutting heads used for intramedullary reaming.

BACKGROUND

Reamers are tools used in orthopedic procedures to cut bone and associated tissue matter. Specifically, the cutting head of the present invention are designed to cut and bore into the intramedullary space or inner canal of a long bone such as a femur, tibia or humerus. Typically, the intramedullary space of a long bone is reamed to clean and create a space for an implant. As such, these reamers are required to be sterile and sharp. Using a dull reamer generates heat that typically leads to tissue necrosis and results in undesirable patient outcomes. A non-sterile reamer blade typically results in an infected and damaged intramedullary space that may lead to other problems for the patient.

Reamers are often used in trauma procedures. In one such procedure, a prosthetic implant is inserted into the intramedullary space to help mend a fractured bone. In the procedure, a flexible reamer is first inserted into the intramedullary space of the fractured bone. Using the intramedullary reamer, a cavity space is then formed for insertion of the implant into the fractured bone.

The preparation of the bone generally consists of removing the interior contents of the bone along its entire length so that a space is created allowing for insertion of the intramedullary nail. The removal of the interior contents occurs in steps, where a cutting head having a relatively small cutting diameter is used to initiate a pilot hole and removal of the medullary contents. A series of cutting heads having progressively larger cutting diameters is then used to further increase the diameter of the intramedullary space and remove more bone and tissue material. The surgeon typically continues to use reamer cutting heads of increasing diameter until the appropriately sized space is created. After the appropriate sized space is created, an intramedullary nail is typically installed within the space to assist in the healing of the traumatized bone.

However, prior art cutting heads have an inefficient blade design which tends to become increasingly dull, particularly when reaming large portions of bone material within a long bone, such as a femur. Furthermore, because of their high cost, traditional cutter heads are typically reused multiple times. Over time, as these reamer heads are used and reused, the cutting blades become dull. As a result, these less efficient prior art cutting heads tend to promote an increase in "head pressure" within the intramedullary canal. "Head pressure" is the pressure that forms ahead of the reaming bone cutter within the intramedullary canal. Increasing head pressure within the intramedullary canal may result in the occurrence of a "fat" embolism. A fat embolism occurs when fat becomes lodged within a blood vessel and obstructs blood flow. The occurrence of a fat embolism may result in a stroke or even death to the patient.

The intramedullary cutting head of the present invention, therefore, is designed to cut bone and tissue more efficiently than the cutting heads of the prior art. In contrast to the prior art, the cutting head blades are designed to reduce reactive torque and axial load while cutting, thus reducing trauma to the bone while cutting within the intramedullary space. In addition, the cutting head of the present invention is designed to efficiently remove cut material and debris so that the debris unobstructedly flows over the cutting head. Thus "head pressure" and the possibility of producing a fat embolism within the intramedullary canal is reduced.

Unfortunately, there is no simple way to evaluate cutting efficiency after these reamer tools have been used and reused. Many times it isn't until the surgeon has reused the reamer numerous times that he becomes aware that the reamer is cutting incorrectly. In many cases, an ineffective, dull, or contaminated reamer tool is not detected until well into the reaming procedure or even after the procedure is complete. Good surgical outcomes are largely dependent on the use of a sharp, sterile reamer that is in optimal condition. Poor surgical outcomes such as a damaged intramedullary space can occur as a result of using dull or contaminated reamers.

Accordingly, the present invention provides an embodiment of a cutting head having a novel blade and assembly design that improves cutting efficiency within the intramedullary space. The enhanced reaming efficiencies of the present invention decrease procedural times and minimize patient trauma. Furthermore, the intramedullary cutting head of the present invention ensures sharpness and cleanliness that promotes optimal patient outcomes.

SUMMARY OF THE INVENTION

The present invention provides an embodiment of a bone cutter for use with an intramedullary reamer. The bone cutter of the present invention is of a unitary body construction that comprises a cutting head having a compound frusto-conical body extending from a proximal barrel portion. The barrel portion comprises a cavity therewithin that is configured to receive a drive shaft.

The cutting head comprises a plurality of cutting blades, each having a tissue cutting edge that extends radially from the compound frusto-conical body. The blades are positioned about the cutting head in a spaced apart manner and designed to increase cutting efficiency and debris removal, thereby reducing reactive torque, axial loading, and head pressure during a surgical procedure. The cutting blades are of a unique compound angle construction that improves cutting efficiency. The cutting blades are oriented at an offset angle with respect to a longitudinal axis of the cutting head. In addition, the tissue cutting edge that extends along each blade is oriented at a cutting angle that is different from the blade offset angle. The angled tissue cutting edge is oriented such that it follows an efficient helical curve as it cuts through bone and tissue.

Moreover, each blade is positioned about the exterior surface of the frusto-conical body at an optimum separation distance between adjacent blades. This optimal separation distance allows for unobstructed removal of intramedullary debris over the cutting head body. The unique blade design of the present invention thus results in increased blade stability, cutting efficiency, and reduced head pressure.

A lumen extends lengthwise along the longitudinal axis through the cutting head. The lumen provides an opening through which debris may be removed from within the intramedullary canal. In addition, the lumen provides an opening through which a guidewire may be positioned therethrough.

In addition, the bone cutter of the present invention may comprise a shaft attachment interface that allows for keyed attachment of the cutting head to a drive shaft. In an embodiment, the shaft attachment interface comprises a drive shaft having an outwardly extending projection. This projection is detachably mated with a proximal cutout portion. The shaft projection is received and mated with the cutout portion of the bone cutter in a keyed relationship. The shaft attachment interface can be provided with a removable interference fit, a locking junction, a dovetail junction or it can be designed as an integral portion of the cutting head and shaft assembly.

Furthermore, a protective sleeve may be removably attached to the proximal end of the cutting head barrel portion. The sleeve provides an alternative means in which to secure a drive shaft to the cutting head. In addition, the sleeve provides a protective covering that minimizes potential disengagement of the shaft from the cutting head. In an embodiment, the sleeve comprises a tapered collar that surrounds the drive shaft and attaches to the barrel portion proximal end.

In an embodiment, the bone cutter of the present invention may be manufactured by a metal injection molding process. In an injection molding process, the bone cutter is fabricated by injecting a composite mixture comprising a powered metal and a binder. The metal injection molding process forms the cutting head and barrel portion having a unitary body construction. Metal injection molding provides a low-cost production process that reduces manufacturing time. In addition, the metal injection molding process avoids the need for expensive grinding operations and assembly of individual blade component pieces.

BRIEF DESCRIPTION OF THE DRAWINGS

FIG. 9 shows an embodiment of a sleeve that may be attached to the cutting head shown in FIG. 1.

FIG. 9A shows a top view of the embodiment of the sleeve shown in FIG. 9.

FIG. 9B is a cross-sectional view of the embodiment of the sleeve shown in FIG. 9 taken along longitudinal axis A-A.

DETAILED DESCRIPTION OF THE PREFERRED EMBODIMENTS

Figure 1:
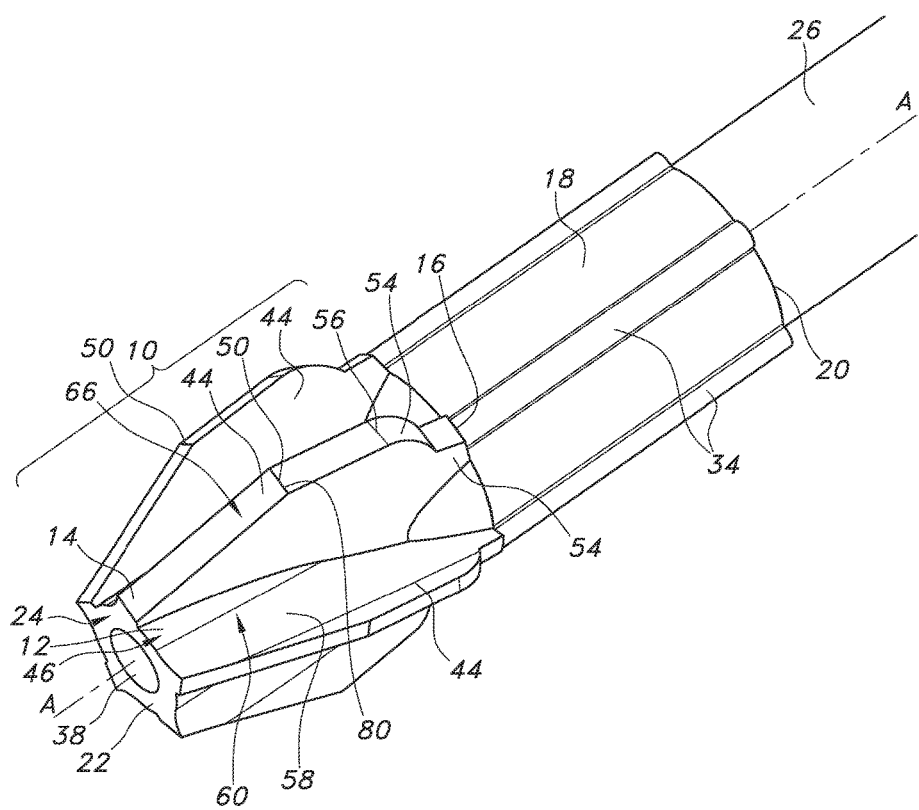
FIG. 1 is a perspective view of an embodiment of the cutting head of the present invention.

Now turning to the figures, FIGS. 1-3, 4, 5, and 6 illustrate an embodiment of a bone cutter comprising a cutting head 10 of the present invention. As shown, the cutting head 10 comprises a frusto-conical body 12 that extends lengthwise along a longitudinal axis A-A from a cutting head distal end 14 to a cutting head proximal end 16. In an embodiment, a barrel portion 18 extends in a proximal direction along longitudinal axis A-A from a barrel portion distal end at the cutting head proximal end 16 to a barrel proximal end 20. In an embodiment, the cutting head 10 comprises a distal end wall 22 having an end wall surface 24. In an embodiment, the end wall surface 24 is oriented perpendicular to longitudinal axis A-A. The cutting head 10 provides for the cutting and removal of bone and tissue from a bone during a surgical procedure, for example, during reaming of an intramedullary canal in a femur. The barrel portion 18 provides for the attachment of the cutting head 10 to a drive shaft 26 (FIG. 1).

Figure 2:
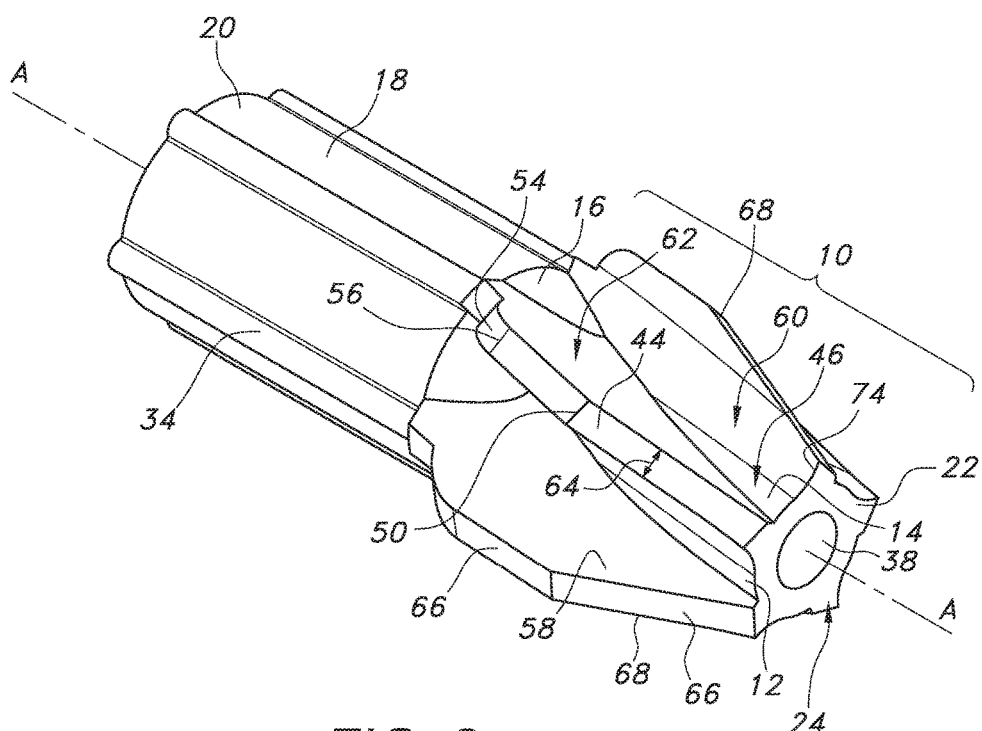
FIG. 2 is an alternate perspective view of the embodiment of the cutting head shown in FIG. 1.
Figure 3:
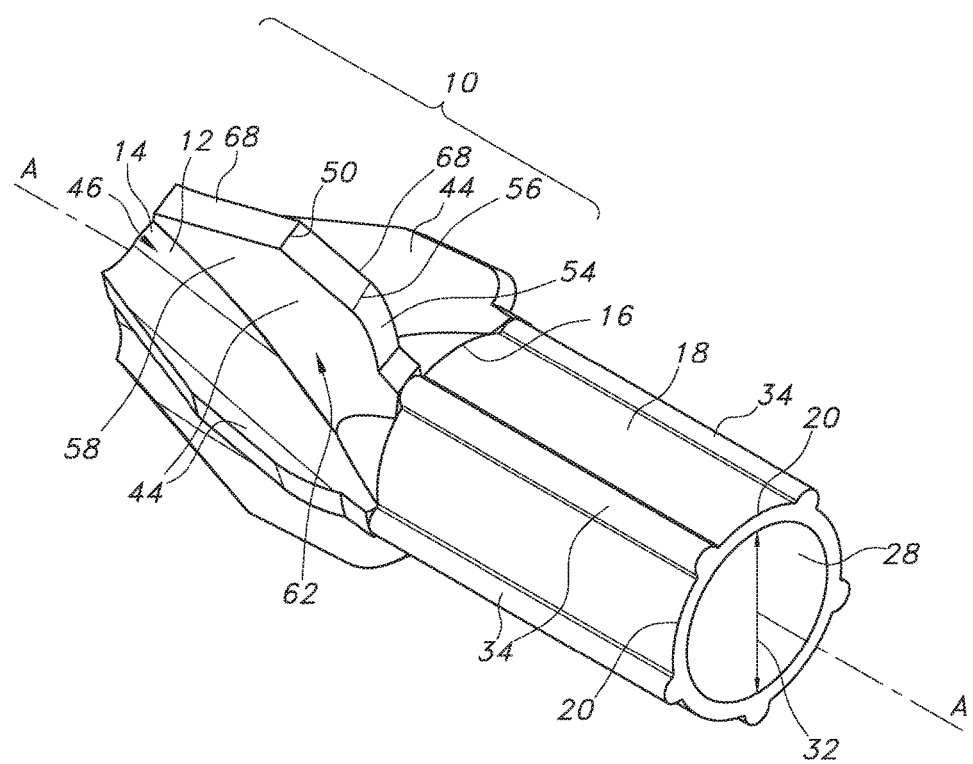
FIG. 3 illustrates a perspective view of the embodiment of the cutting head shown in FIG. 1 taken from the proximal end.
Figure 4:
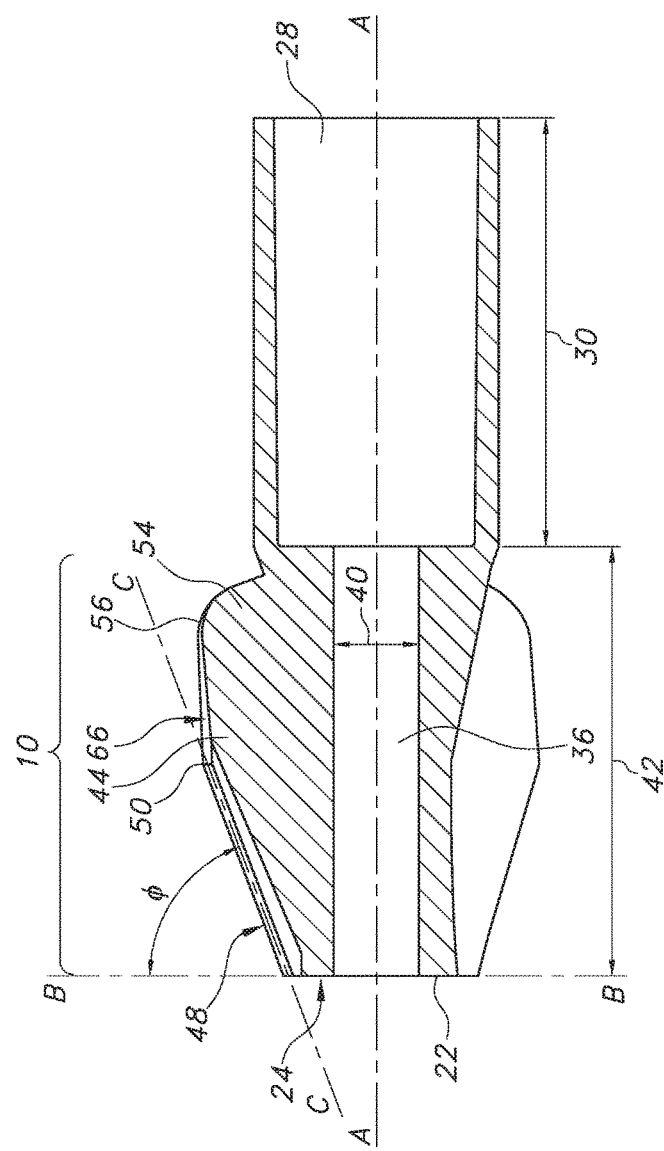
FIG. 4 is a cross-sectional view of the embodiment of the cutting head shown in FIG. 1 taken along longitudinal axis A-A.
Figure 5:
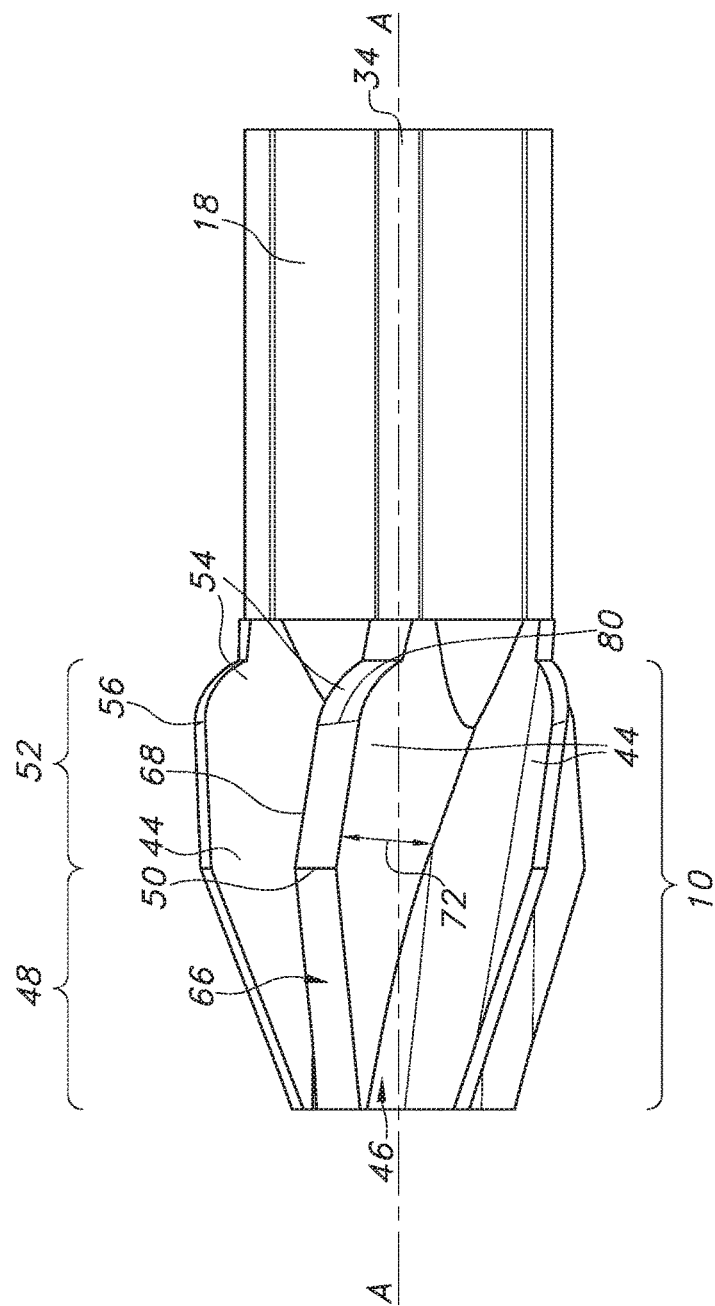
FIG. 5 is a side view of the embodiment of the cutting head shown in FIG. 1.

As shown in FIGS. 2, 3, and 4, a cavity 28, dimensioned to receive the drive shaft 26, extends longitudinally within the barrel portion 18 from the barrel portion proximal end 20 to the cutting head proximal end 16. In an embodiment, the cavity 28 is dimensioned to provide an interference fit with the drive shaft 26. In a preferred embodiment, the cavity 28 has a length 30 that may range from about 0.5 cm to about 2 cm and a diameter (FIG. 2) that ranges from about 0.5 cm to about 1 cm. A plurality of spaced apart ribs 34 may extend longitudinally along the length of the barrel exterior surface.

In addition, a lumen 36 extends along the longitudinal axis A-A through the bone cutting head 10. As illustrated in FIGS. 1 and 3, the lumen 36 extends through the cutting head distal end wall 22, forming a lumen opening 38 therethrough. The lumen 36 extends longitudinally through the cutting head 10 and meets the cavity 28 within the barrel portion 18. The lumen 36 provides a channel for removal of cut bone and tissue from, for example, the intramedullary canal during a surgical procedure. In addition, the lumen 36 provides an opening for a guidewire (not shown) to extend therethrough. The guidewire may be used to help to control movement and positioning of the cutting head 10 within the intramedullary canal. In a preferred embodiment, the lumen 36 has a diameter 40 that ranges from about 0.1 cm to about 1 cm and a length 42 that ranges from about 0.1 cm to about 1 cm.

As illustrated in FIGS. 1-4, 4A, 5, and 6, a plurality of spaced apart blades 44 extend radially from an exterior surface 46 of the frusto-conical body 12. Each of the blades 44 has a distal frusto-conical section 48 that provides for coarse cutting and is delineated by a frusto-conical transition line 50 from a proximal frusto-conical section 52 that provides for fine cutting. As illustrated in FIG. 1, five spaced apart blades 44 are shown. However, the cutting head 10 may be designed with at least two spaced apart blades 44 that extend outwardly from the exterior surface 46 of the frusto-conical body 12. The proximal frusto-conical section 52 extends from the frusto-conical transition line 50 in a proximal direction toward a tail blade segment 54. The proximal frusto-conical section 52 and the tail blade segment 54 meet at a tail blade segment transition line 56 that is positioned proximal of the frusto-conical transition line 50. The tail blade segment 54 extends from the tail blade segment transition line 56 to the cutting head proximal end 16.

As illustrated, each of the blades 44 comprises a cutting sidewall 58 having opposed leading and trailing blade sidewall surfaces 60, 62 that extend outwardly from the exterior surface 46 of the body 12. (The leading sidewall surface 60 will also be referred to hereinafter as the "compound cutting surface 60".) In an embodiment, the outwardly extending leading and trailing surfaces 60, 62 define a blade width 64 therebetween. In a preferred embodiment, the blade width 64 may range from about 0.1 cm to about 0.5 cm. Furthermore, as illustrated, the outwardly extending leading and trailing sidewall surfaces 60, 62 meet at a blade relief surface 66 that extends therebetween. The relief surface 66 extends from the cutting head distal end 14 to the cutting head proximal end 16 along the distal frusto-conical section 48, proximal frusto-conical section 52, and tail blade segments 54.

A tissue cutting edge 68 is formed at the intersection of the leading sidewall surface 60 and the relief surface 66. In an embodiment, the tissue cutting edge 68 extends from the end wall surface 24, along the distal and proximal frusto-conical sections 48, 52 to the tail blade transition line 56. In an embodiment, the cutting head 10 is rotated about the longitudinal axis A-A in either a clockwise or counterclockwise direction. In a preferred embodiment, the cutting head 10 is rotated in a clockwise direction so that the tissue cutting edge 68 leads the trailing sidewall surface 62 as the cutting head 10 is rotated within the intramedullary canal.

In an embodiment, the blades 44 are oriented so that the leading surface 60 of one blade 44 faces the trailing surface 62 of an adjacent blade 44. A gap 70 (FIGS. 6A-6F), forming a clearance space therebetween, resides between two adjacently positioned blades 44. In an embodiment, the gap 70 resides between the leading and trailing sidewall surfaces 60, 62 that are immediately adjacent to each other. In an embodiment, the gap 70 is dimensioned to provide space for the removal of cut bone and tissue during a surgical procedure. In an embodiment, the gap 70 may range from about 0.3 cm to about 2 cm.

Furthermore, the proximal frusto-conical section 52 comprises a height 72 that extends from the exterior surface 46 of the frusto-conical body 12 to the relief surface 66 that extends along the proximal frusto-conical section 52. In an embodiment, the height 72 of the proximal frusto-conical section 52 determines the diameter of the reamed opening created by the cutting head 10 within the intramedullary canal. In an embodiment, the proximal frusto-conical section height 72 may range from about 0.5 cm to about 1 cm.

In an embodiment, the distal frusto-conical section 48 is designed to initially bore into bone, for example, the intramedullary space. The positively sloping relief surface 66 along the distal frusto-conical section 48 is designed to coarsely cut the intramedullary material and move it to the tissue cutting edge 68 along the proximal frusto-conical section 52, which in turn, cuts the intramedullary tissue matter into more finely comminuted matter. The cut material flows over the exterior surface of the cutting head 10 between the gaps 70.

As illustrated in FIG. 4, the tissue cutting edge 68 that extends along the distal frusto-conical section 48 is oriented at a distal frusto-conical section lead-in angle ϕ. The distal frusto-conical section lead-in angle is defined with respect to imaginary plane B-B that is coincident end wall surface 24 and oriented perpendicular to longitudinal axis A-A. In an embodiment, the distal frusto-conical section lead-in angle ϕ extends between imaginary line C-C that is coincident with the tissue cutting edge 68 along the distal frusto-conical section 48, and imaginary plane B-B that is positioned perpendicular to longitudinal axis A-A. In an embodiment, the distal frusto-conical lead-in angle ϕ may range from about 10° to about 80°. In a preferred embodiment, the distal frusto-conical lead-in angle ϕ may range from about 40° to about 70°.

Figure 6:
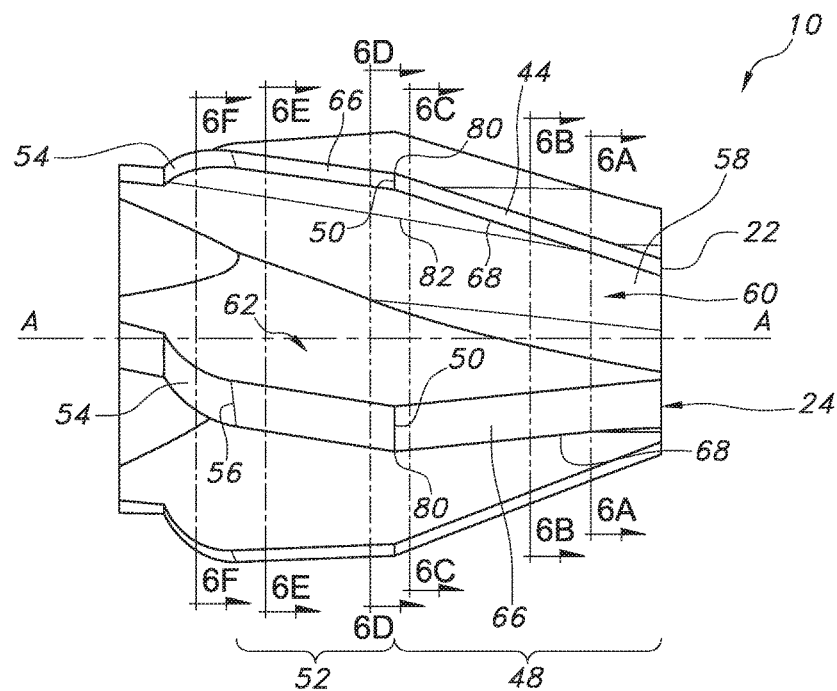
FIG. 6 illustrates a side view of the embodiment of the cutting head shown in FIG. 1.

As illustrated in FIG. 6, the tail segment 54 of each blade 44 of the cutting head 10 further extends distally to the proximal frusto-conical section 52 meeting the distal frusto-conical section 48. The tail segment extends distally from the cutting head proximal end 16. The maximum diameter of the cutting head 10 is at the junction of a distal end of the tail segment 54 and a proximal end of the proximal frusto-conical section 52.

In that manner, the cutting edge 68 in the proximal frusto-conical section 52 extends distally and downwardly toward the longitudinal axis A-A to a frusto-conical transition point 80, which resides along the frusto-conical transition line 50. At this point 80, the incline of the cutting edge 68 in the distal frusto-conical section 48 extends distally and downwardly toward the longitudinal axis A-A at a greater rate than the incline of the cutting edge 68 in the proximal frusto-conical section 52.

Referring back to the drawings, for each cutting blade 44 there is an infinite number of cross-sections from the end wall surface 24 to the frusto-conical transition point 80 of the blade sidewall 58, and then from the transition point 80 to the proximal end of the proximal frusto-conical section 52, FIGS. 6A to 6F being just a few of them. In the cross-sections, an imaginary line D-D extends along the blade relief surface 66. Another imaginary line E-E intersects the longitudinal axis A-A and the outermost endpoint of the cutting edge 68, it being understood that the outermost endpoint of edge 68 is a point in each cross-section. A third imaginary line F-F aligned perpendicular to line E-E extends through the outermost endpoint of the cutting edge 68. A relief angle α is then defined between lines D-D and F-F.

Figure 6A:
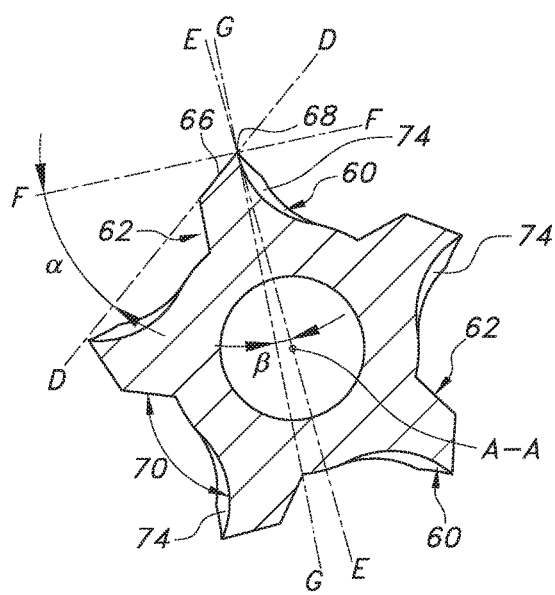
FIGS. 6A-6F are cross-sectional views taken along the longitudinal axis A-A of the cutting head shown in FIG. 1.
Figure 6B:
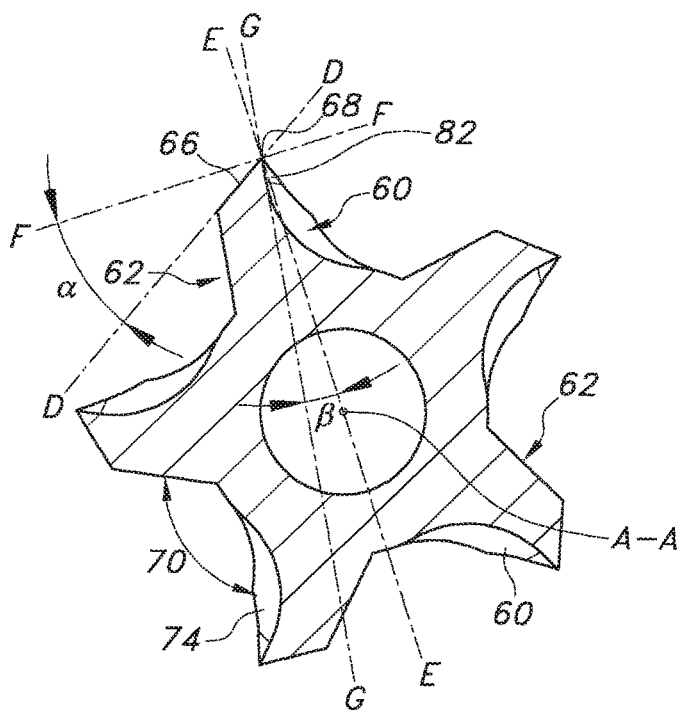
Figure 6C:
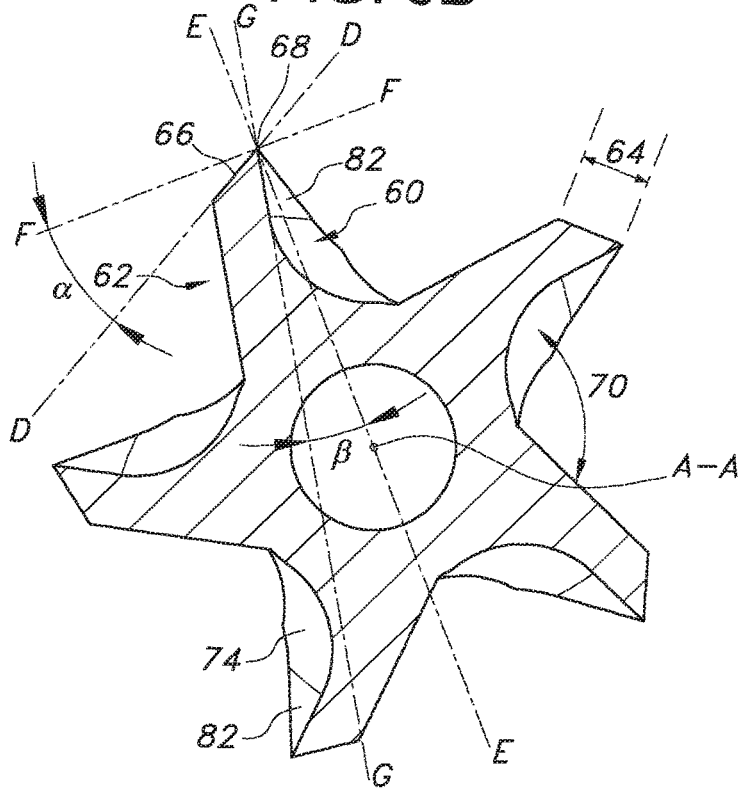

As shown in FIG. 6A, adjacent to, but spaced somewhat proximal the end wall surface 24, the relief angle α is about 35°. FIG. 6B is a cross-section taken about half-way between the end wall surface 24 and the frusto-conical transition point 80 where the relief angle α is about 32°. FIG. 6C is a cross-section taken adjacent to but spaced somewhat distal the frusto-conical transition point 80 where the relief angle is about 28°. Thus, the relief angle α for each of the plurality of cutting blades 44 in the distal frusto-conical section 48 ranges from about 40° at the end wall surface 24 to about 30° at the frusto-conical transition point 80. Furthermore, the average slope of the relief angle within the distal frusto-conical section 48 is about −3.01°/mm from the distal end wall surface 24 to the frusto-conical transition point 80. It is understood that each of the plurality of blades 44 has a similar relief angle at the same cross-section.

Figure 6D:
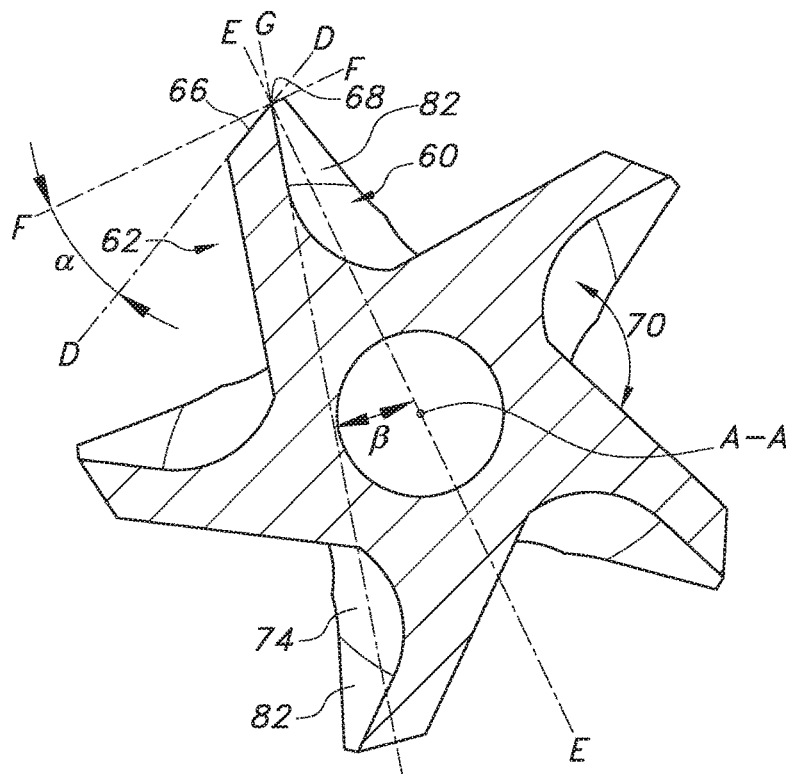
Figure 6E:
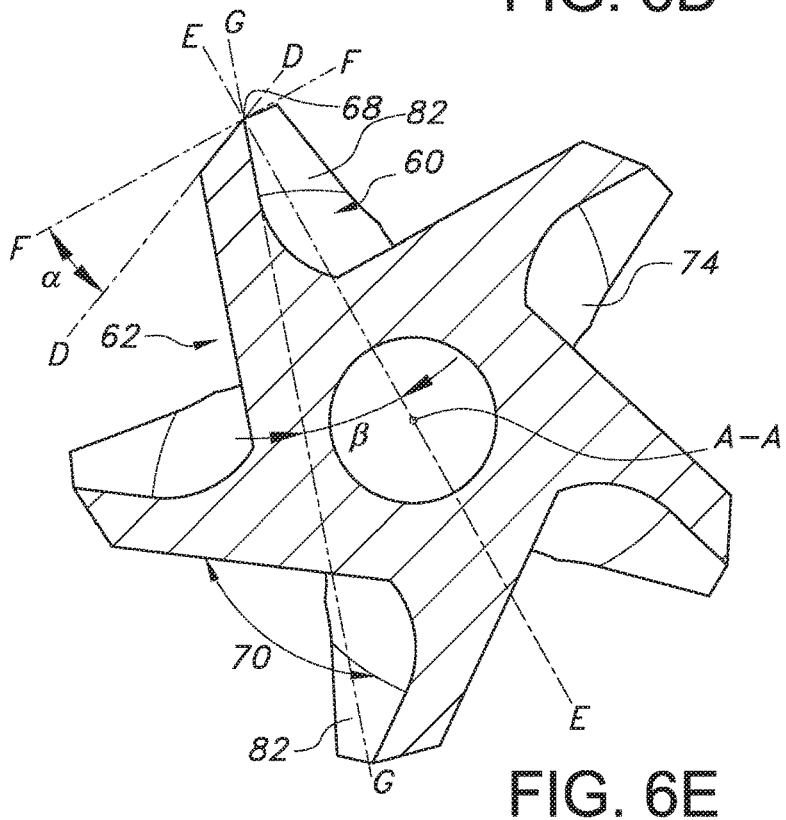
Figure 6F:
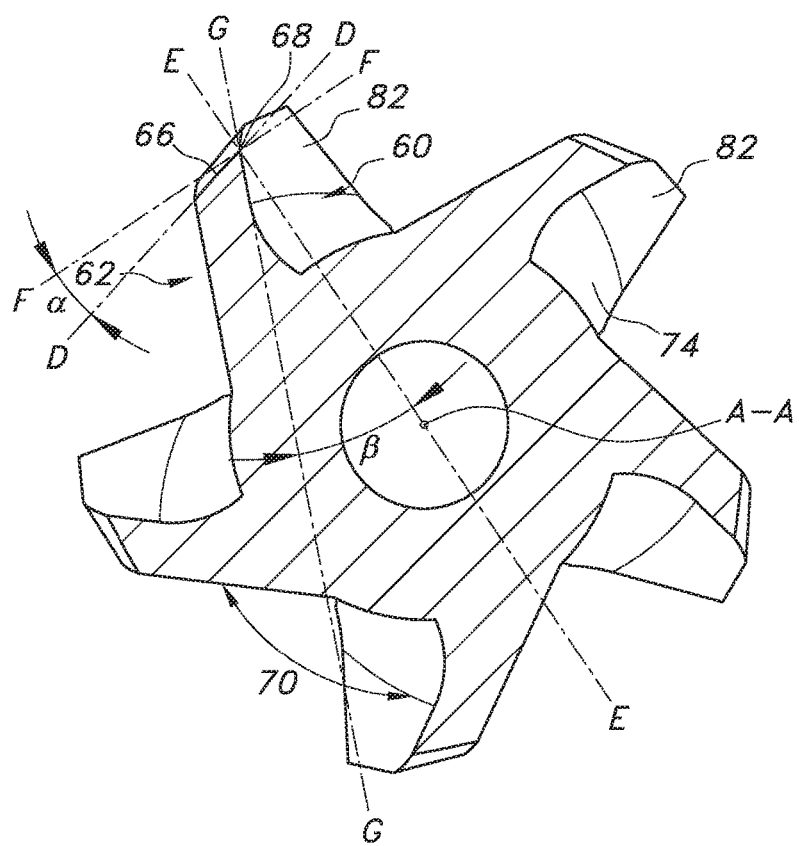

Referring now to the proximal frusto-conical section 52 for each blade 44, the relief angle α is measured in a similar manner as shown in FIGS. 6A to 6C for the relief angle in the distal frusto-conical section 48. In FIG. 6D, the relief angle, again defined as the angle between the imaginary line D-D extending along the blade relief surface 66 and imaginary line F-F aligned perpendicular to line E-E extending through axis A-A and the outermost endpoint of the cutting edge 68, is about 26°. In the cross-section of FIG. 6E, the relief angle is about 21.5°. In FIG. 6F the relief angle is about 14.5°. Thus, the relief angle α gradually declines from a maximum of about 40° at the distal end surface 24 to a minimum of about 21° at the proximal end of the proximal frusto-conical section 52. Furthermore, the average slope of the relief angle α within the proximal frusto-conical section 52 is about −2.22°/mm extending from the frusto-conical transition point 80 to the proximal end of the proximal frusto-conical section 52.

FIGS. 6A to 6F further show that the sidewall 58 for each blade 44 has a leading or partially curved, partially planar compound cutting surface 60 extending proximally from the distal end surface 24 to the proximal end of the proximal frusto-conical section 52. Beginning at the cross-section adjacent the distal end surface 24 and extending proximally, the compound cutting surface 60 gradually changing from a predominantly curved surface 74 to a mostly planar surface 82. Thus, with respect to an orientation extending outwardly along any cross-section that is normal to the longitudinal axis and that intersects the outermost endpoint of the cutting edge 68, and moving axially from the distal end surface 24 to the proximal end of the proximal frusto-conical section 52, the compound cutting surface 60 of sidewall 58 is mostly first curved and then becomes gradually more planar. Thus, a line along a cross-section coinciding with the distal end surface 24 and intersecting the curvature of the curved portion of the cutting surface 60 at a tangent point has the tangent point coinciding with the outermost endpoint of the cutting edge 68, which as defined below equates to a rake angle of 0°. The distal end surface cross-section is the only cross-section in which the line is tangent to the curved portion 74 of the cutting surface 60 of sidewall 58 and coincides with the outermost endpoint of the cutting edge 68. As such, at the distal end surface 24 of the cutting head 10 where the rake angle is 0°, the cutting sidewall surface 60 does not have a planar portion and an imaginary line G-G intersects a tangent point of the curved portion of the tissue cutting edge 68, the tangent point coinciding with the outermost endpoint of the tissue cutting edge 68.

Moving proximally, the compound cutting surface 60 of sidewall 58 has an increasingly larger planer surface portion immediately adjacent to the outermost endpoint of the cutting edge 68. This means that along any one cross-section there is a planar surface portion meeting a curved surface portion at a transition point with this transition point being spaced at greater and greater distances from the outermost endpoint of the cutting edge 68 as the cross-sections are taken more and more proximally. In other words, moving proximally, the transition point between the planar portion of the compound cutting surface 60 and the curved portion of that cutting surface moves closer and closer toward the longitudinal axis and further and further away from the outermost endpoint of the cutting edge 68 until there is substantially no curvature to the cutting surface 60 of the sidewall 58. Instead, the cutting surface 60 of sidewall 58 is generally a planar surface at the proximal end of the proximal frusto-conical section 52.

This is illustrated in FIG. 6A in the distal frusto-conical section 48 where imaginary line G-G intersects at a point where an outer planar portion meets a curved portion of the cutting surface 60 of sidewall 58, this point being spaced from the outermost endpoint of the cutting edge 68. A rake angle β is then defined between line E-E (intersecting the longitudinal axis A-A and the outermost endpoint of the cutting edge 68) and line G-G. In FIG. 6A, the rake angle β is about 5°. In FIG. 6B, which is a cross-section taken about half-way between the end wall surface 24 and the frusto-conical transition point 80, the rake angle β is about 8°. Moving proximally to cross-section FIG. 6C, which is taken adjacent to, but spaced somewhat distal the frusto-conical transition point 80, the rake angle β between line G-G and line E-E is about 12°. Thus, the rake angle β for the cutting surface 60 for each of the plurality of cutting blades 44 in the distal frusto-conical section 48 ranges from about 0° at the end wall surface 24 to about 12° at the frusto-conical transition point 80 of the cutting edge 68. Furthermore, the average slope of the rake angle β, within the distal frusto-conical section 48 is about 2.08°/mm. Again, it is understood that each of the plurality of blades 44 has a similar rake angle at the same cross-section.

Regarding the rake angle β, in the proximal frusto-conical section 52, this angle is measured in a similar manner as shown in FIGS. 6B and 6C for the rake angle in the distal frusto-conical section 48. In FIG. 6D, the rake angle between line E-E (intersecting the longitudinal axis A-A and the outermost endpoint of the cutting edge 68) and line G-G coincident to the planar surface portion of the sidewall 58, is about 13.5°. In FIG. 6E the rake angle is about 18.5°. In FIG. 6F the rake angle is about 22°. Thus, the rake angle β, gradually increases from a minimum of about 0° at the distal end wall surface 24 to a maximum of about 22° at the blade tail transition line 56 within the tail segment 54. It is noted that the average slope of the rake angle β, within the proximal frusto-conical section 52 is about 2.11°/mm.

In an embodiment, the blade tail segment 54 has a curved blade relief surface 66 that extends from the blade tail transition line 56 to the exterior surface 46 of the frusto-conical body 12. Unlike the distal and proximal frusto-conical sections 48, 52, the tail segment 54 is not intended to cut tissue or bone. As illustrated, the proximal blade relief surface 66 is constructed such that it curves downward and away from the tissue cutting edge 68 of the proximal frusto-conical section 52. In an embodiment, the tail segment 54 helps to stabilize the cutting head blade 44 as it reams within the intramedullary canal. The sloping surface of the tail relief surface 66 also enables the reamer to traverse the cut canal when the reamer is extracted.

Figure 7:
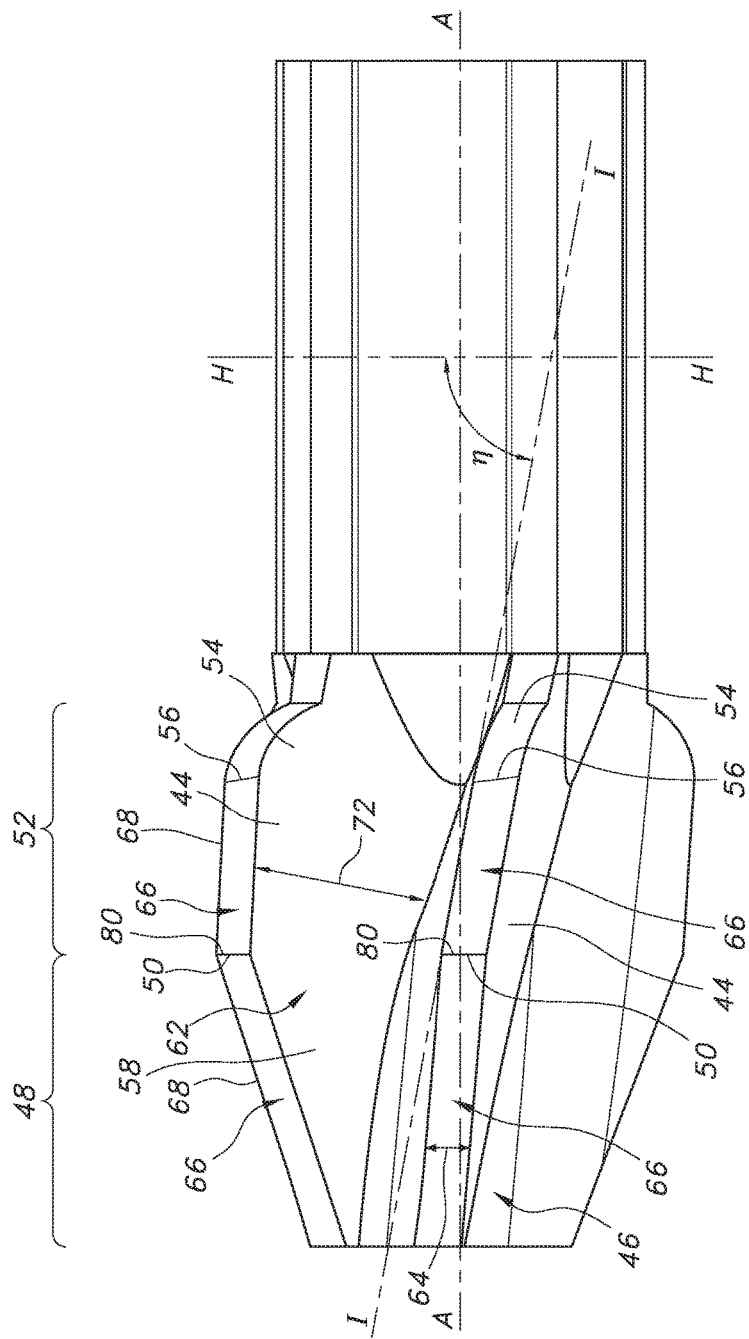
FIG. 7 is a magnified side view of the embodiment of the cutting head shown in FIG. 1.
Figure 8:
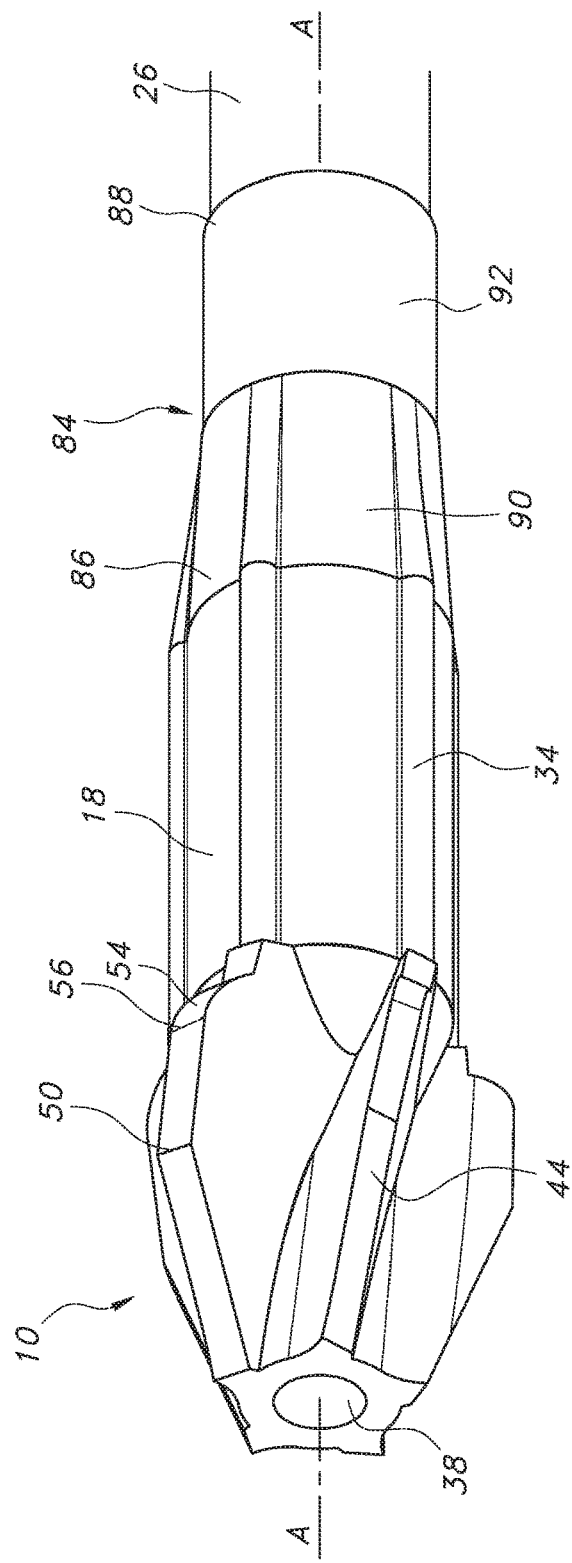
FIG. 8 illustrates an embodiment of a sleeve attached to the cutting head shown in FIG. 1.

FIG. 7 illustrates a magnified side view of an embodiment of the cutting head 10 of the present invention. As shown, imaginary plane H-H is aligned perpendicular to longitudinal axis A-A. In an embodiment, each blade 44 of the cutting head 10 comprises a blade deflection angle η in which the leading surface 60 of the proximal frusto-conical section 52 deflects at an angle from the leading sidewall surface 60 of the distal frusto-conical section 48 at the frusto-conical transition point 80. As illustrated, the blade deflection angle η is defined as the angle that extends between imaginary plane H-H, that lies perpendicular to longitudinal axis A-A and imaginary line I-I that is coincident with the leading sidewall surface 60 of the proximal frusto-conical section 52. In an embodiment, the blade deflection angle η may range from about 70° to about 90°.

In an embodiment, the cutting head 10 and barrel portion 18 may be formed having a unitary body construction. In a preferred embodiment, the cutting head 10 and barrel portion 18 may be formed using a metal injection molding process in which powdered metal such as 17-4 stainless steel mixed with a binder material is injected into a mold that defines the cutting head and barrel portion shape. After the shape of the cutting head and barrel portion are formed within the mold, the molded part is them heat treated at a temperature ranging from about 100° C. to about 1,400° C. While 17-4 stainless steel is a preferred material from which the bone cutter is formed, the bone cutter may also be formed from other metallic material such as, but not limited to, ferrous alloys, aluminum, precious metals, titanium alloys, nickel, nickel-base super alloys, molybdenum, molybdenum-copper, tungsten alloys, cobalt-chromium, carbides, ceramic, and cermets such as Fe—TiC. In addition, the cutting head 10 and barrel portion 18 may also be formed from polymeric material materials, such as but are not limited to, polyetheretherketone (PEEK), polyacrylamide (PARA) and acrylonitrile butadiene styrene (ABS).

FIGS. 8, 9, 9A, and 9B illustrate an embodiment of an optional sleeve 84 having spaced apart distal and proximal sleeve ends 86, 88. The sleeve distal end 86 may be removably attached to the proximal end of the cutting head 10. In an embodiment, the sleeve 84 forms a transition between the barrel portion proximal end 20 and the drive shaft 26. The sleeve 84 is constructed to provide an improved seal between the drive shaft 26 and the cutting head 10. Furthermore, the sleeve 84 is designed to minimize the possibility that the junction between the cutting head 10 and drive shaft 26 at the barrel proximal end 20 may obstruct insertion or removal of the cutting head 10 within the intramedullary canal.

In an embodiment, the sleeve 84 comprises a collar 90 that extends to a tube portion 92. The collar 90 has a tapered construction comprising a distal end outer diameter 98 that is greater than a proximal end outer diameter 100. As shown, the tube portion 92 comprising a tube outer diameter 102 and a tube inner diameter 104 that extends along longitudinal axis A-A from the collar proximal end 96. The collar distal end 94 is dimensioned to receive the barrel proximal end 20. In an embodiment, the collar 90 may comprise a chamfer 106 that is formed within the collar interior at the collar distal end 94. In an embodiment, the chamfer 106 extends annularly about the interior of the collar distal end 94. In an embodiment, the chamfer 106 forms a surface that is configured to physically contact the proximal end of the barrel portion 18. An adhesive positioned along the chamfer surface may be used to connect the barrel portion 18 to the sleeve 84.

In an embodiment, the collar proximal end outer diameter 100 is greater than the tube portion outer diameter 102. This preferred relationship between the two diameters of the collar and tube portions allows for an annular ledge 108 to be formed at the collar proximal end 96. In addition, a plurality of spaced apart collar ribs 110 may extend longitudinally along the collar exterior surface. These collar ribs 110 are dimensioned similarly to the exterior ribs that extend along the barrel portion exterior surface. In an embodiment, a ring 112, such as a ring of shrink wrap or other compression material, may be positioned around the tube outer diameter 102. As such, the ring 112 is designed to constrict the tube portion 92 around the shaft 24 positioned within the tube 92, thereby forming an interference fit therebetween.

Figure 10:
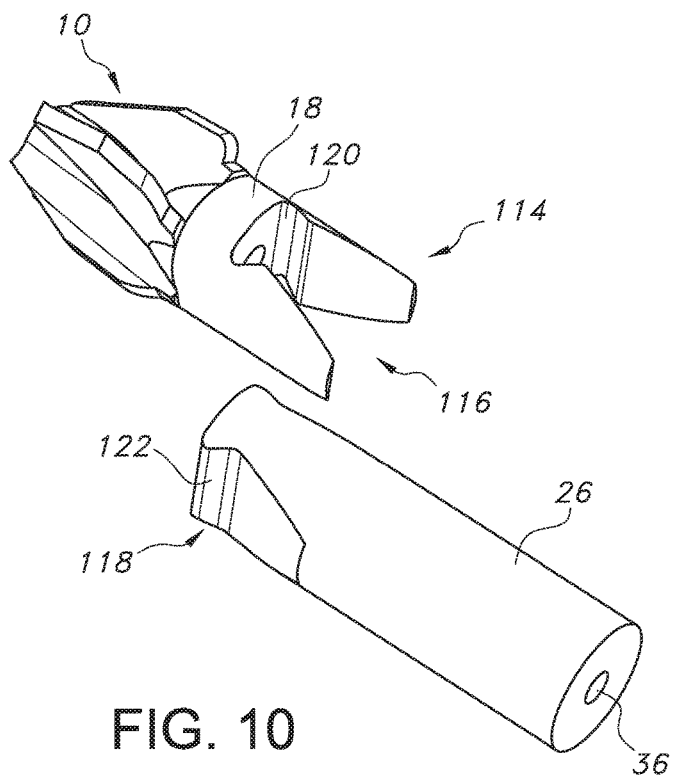
FIGS. 10 and 11 illustrate an embodiment of a shaft attachment interface that may be used to attach a drive shaft to the cutting head shown in FIG. 1.
Figure 11:
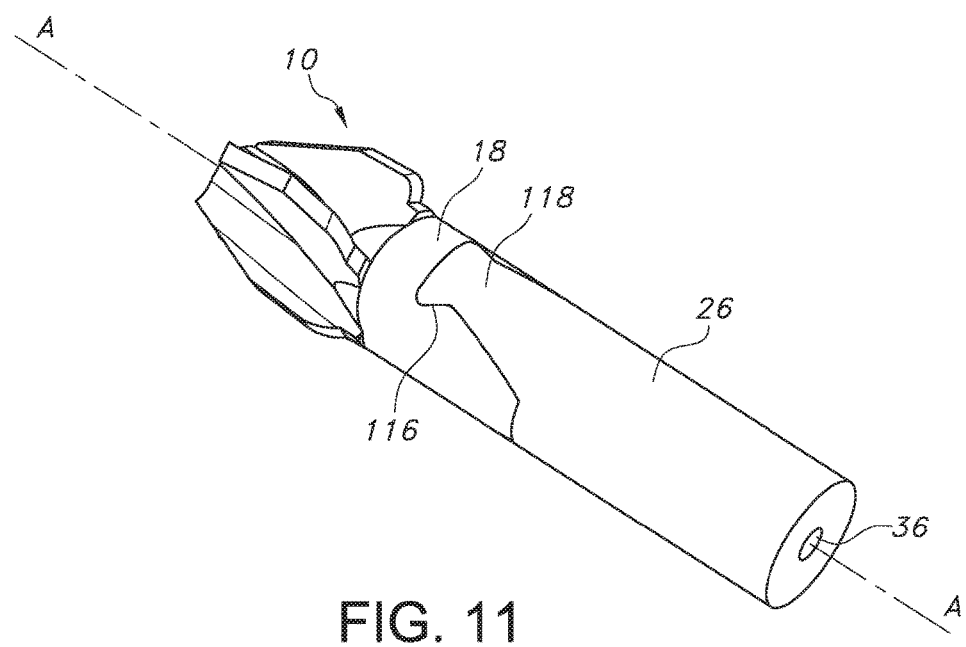

FIGS. 10 and 11 illustrate an embodiment of a shaft attachment interface 114 which may be used to attach the shaft 24 to the cutting head 10. As illustrated, the shaft attachment interface 114 may comprise a cutout portion 116 that is designed to receive a projection 118 having a corresponding cross-sectional shape in a keyed mated interface. In an embodiment, the projection 118, constructed at the shaft distal end, is designed to be received within the cutout portion 116 having a corresponding cross-sectional shape, within a portion of the barrel 18. The projection 118 may be received within the cutout portion 116 in a dovetail relationship. In the embodiment shown in FIG. 11, the cutout portion 116 may comprise at least one groove 120 that is formed within the sidewall of the barrel 18 and that extends perpendicular to the longitudinal axis. A ridge 122 that corresponds to the dimension of the groove 120 extends outwardly from the shaft distal end. As shown in FIG. 10, the ridge 122 formed at the distal end of the drive shaft is received within the groove 120 formed within the barrel sidewall in a mated dovetail relationship.

In an embodiment, the cutout portion 116 and the corresponding shaped projection 118 are not limited to the embodiment illustrated in FIGS. 10 and 11. It is further contemplated that the cutout portion 116 formed within the barrel portion 18 may be constructed of a plurality of non-limiting shapes such that the shaft distal end is formed of a corresponding shape that is capable of being received in a mated relationship therewithin. For example, the cutout portion 116 may be of a cross-sectional shape having a curved geometry, a rectangle geometry, triangular geometry or star geometry. It is also contemplated that that cutout portion 116 may be formed within the shaft distal end and the corresponding shaped projection 118 is formed extending from the barrel proximal end 20.

Thus, it has been shown that the reamer cutting head of the present invention provides for a low cost flexible single use intramedullary cutting tool. The present invention does not require additional grinding or re-sharpening procedures which ensures optimal sharpness and sterilization. The features of the present invention provide for an efficient intramedullary cutting tool with an optimized cutting design that enhances reaming efficiency and effectiveness.

What is claimed is:

1. A bone cutter configured for detachable connection to a source of rotary motion, the bone cutter comprising:
   a) a cutting head extending distally along a longitudinal axis from a proximal end to a distal end surface; and
   b) at least two spaced apart cutting blades supported by the cutting head, each cutting blade comprising a relief surface residing between opposed cutting and trailing sidewall surfaces, wherein a tissue cutting edge resides at an intersection of the cutting sidewall surface and the relief sidewall surface, the tissue cutting edge having a frusto-conical shape extending distally and downwardly toward the distal end surface of the cutting head,
   c) wherein, with respect to any one cross-section aligned normal to the longitudinal axis and taken adjacent the distal end surface of the cutting head to a proximal end of the cutting blade,
      i) the tissue cutting edge comprises
         A) a first imaginary line that is coincident the blade relief surface;
         B) a second imaginary line that intersects the longitudinal axis and an outermost endpoint of the tissue cutting edge;
         C) a third imaginary line that is normal to the second imaginary line and intersects the outermost endpoint of the tissue cutting edge; and
         D) a relief angle defined between the first imaginary line and the third imaginary lines ranges from about 40° adjacent the distal end surface of the cutting head to about 21° at the proximal end of the cutting blade; and
      ii) the cutting sidewall surface has a planar cutting surface portion extending from the tissue cutting edge toward the longitudinal axis to a transition point where the planar cutting surface portion meets a curved cutting surface portion of the cross-section so that with respect to the any one cross-section, the cutting sidewall surface comprises
         A) a fourth imaginary line that intersects the transition point and the outermost end point of the tissue cutting edge; and B) a rake angle defined between the second imaginary line and the fourth imaginary lines that ranges from about 5° adjacent the distal end surface of the cutting head to about 19° at a proximal end of the frusto-conical shape of the tissue cutting edge; and d) wherein, with respect to a cross-section aligned normal to the longitudinal axis and taken at the distal end surface of the cutting head,
   i) the rake angle defined between the second imaginary line and the fourth imaginary lines is 0°; and
   ii) the cutting sidewall surface does not have the planar cutting surface portion; and e) a proximal barrel portion of the cutting head, the barrel portion having a cavity that is configured to detachably receive a drive shaft.

2. The bone cutter of claim 1, wherein the tissue cutting edge comprises a proximal frusto-conical portion meeting a distal frusto-conical portion at a frusto-conical transition point, the proximal frusto-conical portion extending downwardly and distally toward the longitudinal axis at a proximal portion slope and the distal frusto-conical portion extending downwardly and distally toward the longitudinal axis at a distal portion slope that is greater than the proximal portion slope.

3. The bone cutter of claim 2, wherein, with respect to the longitudinal axis, a maximum outer radius of each of the at least two cutting blades is at a proximal end of the proximal frusto-conical portion.

4. The bone cutter of claim 2, wherein a proximal relief angle in the proximal frusto-conical portion ranges from about 20° to about 28° at the frusto-conical transition point, and a distal relief angle in the distal frusto-conical portion ranges from about 28° to about 40° at the distal end surface of the cutting head.

5. The bone cutter of claim 4, wherein the proximal relief angle in the proximal frusto-conical portion has a proximal relief angle slope of about −2.22°/mm extending downwardly and distally toward the longitudinal axis and the distal relief angle in the distal frusto-conical portion has a distal relief angle slope of about −3.01°/mm extending downwardly and distally toward the longitudinal axis.

6. The bone cutter of claim 2, wherein a proximal rake angle in the proximal frusto-conical portion of the tissue cutting edge ranges from about 12° to about 20° at the transition point and a distal rake angle in the distal frusto-conical portion of the tissue cutting edge ranges from about 20° to about 0° at the distal end surface of the cutting head.

7. The bone cutter of claim 6, wherein the proximal rake angle in the proximal frusto-conical portion has a proximal rake angle slope of about 2.11°/mm and the distal rake angle in the distal frusto-conical portion has a distal rake angle slope of about 2.08°/mm.

8. The bone cutter of claim 1, wherein, with a first cross-section being coincident the distal end surface of the cutting head and at a second cross-section being proximal the first cross-section, the transition point is spaced a first distance from the outermost endpoint of the tissue cutting edge, and at a third cross-section proximal the second cross-section, the transition point is spaced a second distance from the outermost endpoint of the tissue cutting edge, the second distance being greater than the first distance.

9. The bone cutter of claim 1, including a proximal cutout portion of the cutting head, the cutout portion having a cross-sectional geometry oriented perpendicular to the longitudinal axis, and wherein the cutout portion is configured to detachably receive a projection of a drive shaft.

10. The bone cutter of claim 1, further comprising a collar that is connectable to a drive shaft, the collar having a collar proximal end extending along the longitudinal axis to a collar distal end connected to the barrel portion, wherein the collar proximal end has a first outer diameter and the collar distal end has a second outer diameter, the first outer diameter being less than the second outer diameter to thereby provide for securely connecting the bone cutter to a drive shaft.

* * * * *